United States Patent [19]

Liu et al.

[11] 4,410,712
[45] Oct. 18, 1983

[54] ANTIBIOTICS X-14873 A, G AND H

[75] Inventors: Chao-min Liu, Cedar Grove, N.J.; Homer D. Tresner, La Farge, Wis.; John Westley, Cedar Grove, N.J.

[73] Assignee: Hoffmann-La Roche Inc., Nutley, N.J.

[21] Appl. No.: 356,654

[22] Filed: Mar. 10, 1982

[51] Int. Cl.³ .......................................... C07D 309/06
[52] U.S. Cl. ................................. 549/414; 424/283; 435/118; 435/253
[58] Field of Search ........................................ 549/414

[56] References Cited
U.S. PATENT DOCUMENTS

| | | | |
|---|---|---|---|
| 3,944,573 | 3/1976 | Westley et al. | 549/414 |
| 3,950,320 | 4/1976 | Stempel et al. | 549/414 |
| 4,083,968 | 4/1978 | Westley | 549/414 |
| 4,168,272 | 9/1979 | Westley | 549/414 |
| 4,193,928 | 3/1980 | Coffen | 549/414 |

*Primary Examiner*—Nicky Chan
*Attorney, Agent, or Firm*—Jon S. Saxe; Bernard S. Leon; Frank P. Hoffman

[57]    ABSTRACT

There are provided antibiotics X-14873 A, G and H of the formulas

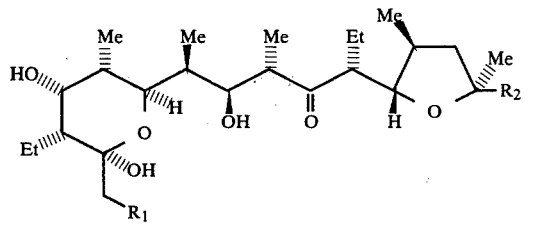

wherein for X-14873A, $R_1$ is $CO_2H$ and $R_2$ is for X-14873G, $R_1$ is hydrogen and $R_2$ is

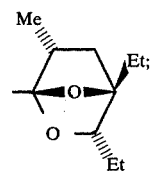

and for X-14873H, $R_1$ is hydrogen and $R_2$ is

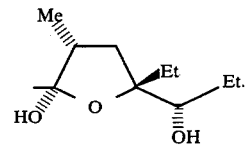

The compounds exhibit antibiotic activity. Also disclosed is a process to produce the above compounds.

3 Claims, No Drawings

ANTIBIOTICS X-14873 A, G AND H

DESCRIPTION OF THE INVENTION

The present invention relates to Antibiotics A, G, and H of the formula

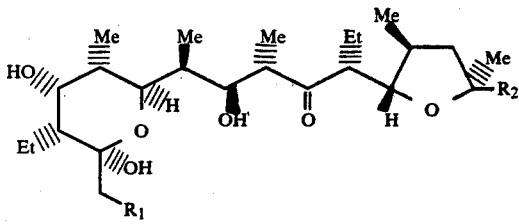

wherein for X-14873A, $R_1$ is $CO_2H$ and $R_2$ is

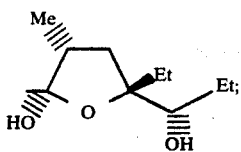

for X-14873G, $R_1$ is hydrogen and $R_2$ is

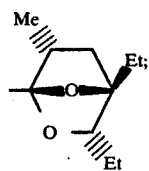

and for X-14873H, $R_1$ is hydrogen and $R_2$ is

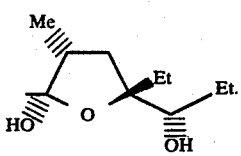

Also included within the scope of the present invention are the pharmaceutically acceptable salts thereof.

As utilized in the structural formulas herein the expression Me stands for methyl and Et stand for ethyl.

There is further provided, according to the present invention, a fermentation process for the production of such antibiotic substances together with the isolation techniques utilized to recover the antibiotic compound from the fermentation broth. In addition, the isolation of three novel actinomycins, X-14873 B, C and D, is described.

The organism producing the antibiotics of the present invention is a new species designated Streptomyces sp. X-14873. A culture of the living organism, given the laboratory designation X-14873 has been deposited in the American Type Culture Collection, Rockville, Md. and added to its permanent collection of microorganisms as ATCC 31679. The new microorganism was isolated from a soil sample near sagebrush in Crandall Creek, Wyoming.

Growth Characteristics

The organism was cultivated on the standard ISP media (Difco) described by Shirling and Gottlieb "Methods for Characterization of Streptomyces Species", Intern. J. System. Bacteriol., 16, pp 313–340, 1966

Media utilized in other tests were those from the following references:

| | Test | References |
|---|---|---|
| A. | Sodium Chloride tolerance | Gordon and Smith "Rapidly |
| B. | Hydrolysis of casein | Growing Acid Fast |
| C. | Reduction of nitrate | Bacteria", J. Bacteriol., 66:41–48, 1953 |
| D. | Gelatin (modified with nutrient gelatin (BBL) plus 2.00% agar in place of meat infusion agar) | Skerman, "A Guide to the Identification of the Genera of Bacteria", Williams and Williams Co., Baltimore, 1967. |
| E. | Starch (Actinomyces broth [Difco] plus 0.25% soluble starch and 2.0% agar) | |
| F. | Decomposition of adenine, xanthine, tyrosine and hypoxanthine | Gordon, "The taxonomy of soil bacteria", p. 293–321, Gray and Parkinson, Ecology of Soil Bacteria, Liverpool Press, Liverpool, England. |

Tests were run at 28° and 37° C. for almost all media. Color determinations were made after 2 and 4 weeks of incubation. Pigmentation was described by using the color scheme in the Color Harmony Manual, 4th ed., 1958.

Carbon utilization was determined by the method of Shirling and Gottlieb (above) using ISP-9 (Difco) medium.

A 48 hour-old ISP-1 broth culture of X-14873 was centrifuged and homogenized to obtain a washed suspension for inoculation.

The ability of the organisms to grow at 10°, 28°, 37°, 45° and 50° C. was investigated by inoculating broth of ISP-1 (Difco) medium. Cell wall analysis of the isomer of diaminopimelic acid was performed by the method of Becker et al., Appl. Microbiol., 12, 421–423, 1964.

Results

Microscopic Examination

Strain X-14873 produces a substrate mycelium which does not fragment into spores and an aerial mycelium, forming rectus-flexibilis spore chains with 10–20 spores per chain. Spores are smooth and range in size from 1.0×0.52 μm to 1.25 to 0.75 μm.

Cell Wall Analysis

The cell wall contains the LL-isomer of diaminopimelic acid which, together with the above microscopic examination, places this organism in the genus Streptomyces.

Macroscopic Examination

Table 1 summarizes the amount of growth, degree of sporulation, spore mass color, color of reverse-substrate mycelium and presence of soluble pigment produced by strain X-14873 on various agar media.

Physiological Characteristics

Strain X-14873 hydrolyzes casein, starch, gelatin, adenine, xanthine, hypoxanthine, tyrosine and urea. Table 2 compares the carbon utilization characteristics of strain X-14873 with those of *Streptomyces chrysomallus, Streptomyces parvus* and *Streptomyces globisporus* chosen for their similarity in morphological and physiological characteristics.

Further metabolic and morphological characteristics are set forth in Table 3 below.

TABLE 1

Cultural characteristics of strain X-14873

| Agar Medium | Amount of Growth Degree of Sporulation | Spore Mass Color | Color of Reverse Substrate Mycellium |
|---|---|---|---|
| Yeast-malt extract (ISP2) | moderate to abundant growth; moderate sporulation; brown soluble pigment | c(light gray) where sporulated; 3ni(clove brown) where not sporulated | 3ie(camel) and 2gc(light tan) at edge |
| Oatmeal (ISP3) | moderate growth; sparse sporulation; yellow soluble pigment | b(oyster white) where sporulated; 2gc (bamboo) where not sporulated | 2ec(biscuit) |
| Inorganic salts-starch (ISP4) | abundant growth; well sporulated; hydrolyzes starch; yellow soluble pigment | 3cb(sand) | 3lc(amber) and 3le(cinnamon) |
| Glycerol-Asparagine (ISP5) | moderate growth; moderate sporulation; yellow-brown soluble pigment; hygroscopic | b(oyster white) | 3le(cinnamon) |
| Czapek-Dox | moderate growth; moderate sporulation; yellow soluble pigment; slightly hygroscopic | b(oyster white) | 2ic(honey gold) |

TABLE 3

| Test | Result |
|---|---|
| Spore mass color | gray(yellowish) |
| ISP6, darkening | — |
| Melanin, ISP7 | — |
| ISP1, darkening | — |
| Casein hydrolysis | + |
| Starch hydrolysis | + |
| NaCl(%) tolerance | 5 |
| Growth range temp(°C.) | 10–28° |
| Reverse-side pigment | — |
| Soluble pigment | yellow |
| Streptomycin sensitivity (10 mcg in ¼" disc) | +13mm |
| Lysozyme sensitivity | + |
| Nitrate reduction | + |
| Hygroscopic property | + |
| Antibiotic Production | Antibiotic X-14873A |
| | Antibiotic X-14873G |
| | Antibiotic X-14873H |
| | Actinomycin X-14873B |
| | Actinomycin X-14873C |
| | Actinomycin X-14873D |

TABLE 2

Comparison of carbon utilization by strain X-14873 and related strains

| Carbon source | X-14873 | S. chrysomallus 3194A | S. parvus 3195A | S. globisporus 3201A |
|---|---|---|---|---|
| No carbon control | — | — | — | — |
| D-Glucose | ++ | ++ YS | ++ YS | ++ YS |
| D-Xylose | ± | + | ++ YS | + |
| L-Arabinose | + | + | +(+) | + |
| L-Rhamnose | ++ YS | ++ YS | ++ | ++ |
| D-Fructose | ++ | ++ | ++ | ++ |
| D-Galactose | ++ | ++ YS | ++ YS | ++ |
| Raffinose | ± | — | — | — |
| D-Mannitol | ++ YS | ++ YS | ++ YS | ++ |
| i-Inositol | ± | — | — | — |
| Salicin | + | ± | ± | ± |
| Sucrose | — | — | — | — |
| Cellulose | — | — | — | — |
| Maltose | — | ++ YS | ++ intense YS | ++ |
| Glycerol | ++ | ++ | ++ intense YS | ++ |
| Starch | ++ | ++ YS | ++ | ++ |
| Ribose | ++ | ++ YS | ++ YS | ++ YS |

[a] —: Negative response; ±: doubtful response; +: more growth than on carbon control but less than on glucose; +(+): positive response, nearly equal to growth on glucose; ++: positive response equal to growth on glucose. YS = yellow soluble pigment.

Discussion and Conclusion

Streptomyces strain X-14873 resembles *S. chrysomallus, S. parvus,* and *S. globisporus*. All but *S. globisporus* produce actinomycin. The three known cultures were also tested for production of hydroxylysocellin. In a bioautogram vs. Bacillus sp. (ATCC 27860), both *S. chrysomallus* and *S. parvus* produced activity at a similar $R_F$ in the two different solvent systems.

The known cultures possess a yellow-colored spore mass, while X-14873 is mainly gray with only a hint of yellow. Strain X-14873 produces a yellow soluble pigment as do the other strains. The carbon utilization patterns are very similar for all the strains, except X-14873 does not utilize maltose. Since the cultures all hydrolyze starch, gelatin, casein, and urea, and decompose adenine, xanthine, hypoxanthine, and tryosine, it would be difficult to distinguish between all these cultures.

Strain X-14873 cannot be assigned to a particular species, but instead resembles a group which could be called the *Streptomyces chrysomallus-S. parvus* group based on similarity in antibiotic, yellow soluble pigment production, and carbon utilization pattern.

The strain Streptomyces X-14873 described herein includes all strains of Streptomyces which form the compounds X-14873A, B, C, D, G and H and which cannot be definitely differentiated from the culture number X-14873 and its subcultures, including mutants and variants.

Streptomyces sp. X-14873 when grown under suitable conditions, produces a compound of Formula I. A fermentation broth containing Streptomyces X-14873 is prepared by inoculating spores or mycelia of the organism producing the compound of Formula I into a suitable medium and then cultivating under aerobic conditions. For the production of a compound of the Formula I, cultivation on a solid medium is possible, but for production in large quantities, cultivation in a liquid medium is preferable. The temperature of the cultivation may be varied over a wide range, 20°–35° C., within which the organism may grow, but a temperature of 26°–30° C. and a substantially neutral pH are preferred. In the submerged aerobic fermentation of the organism for the production of a compound of the Formula I, the medium may contain as the source for carbon a commercially available glyceride oil or a carbohydrate such as glycerol, glucose, maltose, lactose, dextrin, starch, etc. in pure or crude states and as the source of nitrogen, an organic material such as soybean meal, distillers' solubles, peanut meal, cotton seed meal, meat extract, peptone, fish meal, yeast extract, corn steep liquor, etc. and when desired, inorganic sources of nitrogen such as nitrates and ammonium salts and mineral salts such as ammonium sulfate, magnesium sulfate and the like. It also may contain sodium chloride, potassium chloride, potassium phosphate and the like and buffering agents such as sodium citrate, calcium carbonate or phosphates and trace amounts of heavy metal salts. In aerated submerged culturing procedures, an anti-foam agent such as liquid paraffin, fatty oils or silicone compounds is used. More than one kind of carbon source, nitrogen source or anti-foam source may be used for production of a compound of the Formula I.

Considered within the ambit of the present invention are the organic or inorganic pharmaceutically acceptable salts of the compound of Formula I. These salts are prepared from the free acid by methods well known in the art—for example, by washing the free acid in solution with a suitable base or salt. Examples of such pharmaceutically acceptable basic substances capable of forming salts for the purpose of the present invention include alkali metal bases such as sodium hydroxide, potassium hydroxide, lithium hydroxide and the like alkaline earth metal bases such as calcium hydroxide, barium hydroxide and the like, and ammonium hydroxide. Alkali metal or alkaline earth metal salts suitable for forming pharmaceutically acceptable salts can include anions such as carbonate, bicarbonate and sulfates. Preferred for use in this invention are salts formed from alkali metal bases.

Examples of organic bases forming pharmaceutically acceptable salts with the compound of Formula I are lower alkyl amines, primary, secondary and tertiary hydroxy-lower alkylamines such as ethylamine, isopropylamine, diethylamine, methyl-n-butylamine, ethanolamine and diethanolamine.

The following examples serve to illustrate this invention without limiting it thereto:

EXAMPLE 1

Shake-flask Fermentation

The Streptomyces X-14873 culture is grown and maintained on a starch-casein agar slant having the following composition (grams/liter distilled water):

| | |
|---|---|
| Soluble starch | 10.0 |
| Casein | 1.0 |
| $K_2HPO_4$ | 0.5 |
| $MgSO_4$ (anhydrous) | 0.5 |
| Agar | 20.0 |
| The medium pH is adjusted to 7.4 with NaOH before autoclaving. | |

The slant is inoculated with X-14873 culture and incubated at 28° C. for 7–14 days. A chunk of agar containing spores and mycelia from the sporulated culture is used to prepare vegetative inoculum by inoculating a 500-ml Erlenmeyer flask containing 100 ml of inoculum medium having the following composition (grams/liter distilled water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 |
| pH is adjusted to 7.0 before sterilization. | |

The inoculated inoculum medium is incubated at 28° C. for 72 hours on a rotary shaker, operating at 250 rpm with a 2-inch stroke.

A 30 ml portion of the resulting culture is then used to inoculate a 6-liter Erlenmeyer flask containing 1.25 liter sterilized production medium having the following composition (grams/liter distilled water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 |

-continued

| | |
|---|---|
| pH is adjusted to 7.0 before sterilization. | |

The inoculated medium is incubated at 28° C. for 5 days on a rotary shaker running at 250 rpm with a 2-inch stroke.

EXAMPLE 2

Tank Fermentation

The Streptomyces X-14873 culture is grown and maintained on a starch-casein agar slant having the following composition (grams/liter distilled water):

| | |
|---|---|
| Soluble starch | 10.0 |
| Casein | 1.0 |
| $K_2HPO_4$ | 0.5 |
| $MgSO_4$ | 0.5 |
| Agar | 20.0 |
| pH is adjusted to 7.4 with NaOH before autoclaving. | |

The slant is inoculated with X-14873 culture and incubated at 28° C. for 7-14 days. A chunk of agar containing spores and mycelia from the sporulated culture is used to prepare vegetative inoculum by inoculating a 500-ml Erlenmeyer flask containing 100 ml of inoculum medium having the following composition (grams/liter distilled water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 |
| pH is adjusted to 7.0 with NaOH before sterilization. | |

The inoculated medium is incubated for 72 hours at 28° C. on a rotary shaker operating at 250 rpm, 2-inch stroke.

Twenty ml (1%, v/v) of this culture are used to inoculate a 6-liter Erlenmeyer flask containing 2 liters of medium having the following composition (grams/liter distilled water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 |
| pH is adjusted to 7.0 before autoclaving at 15-20 pound pressure for 45 minutes. | |

The inoculated medium is incubated for 72 hours at 28° C. on a rotary shaker operating at 250 rpm.

Four liters of this culture are used to inoculate 60 gallons of the following medium in a 100 gallon fermentor (grams/liter tap water):

| | |
|---|---|
| Tomato pomace | 5.0 |
| Distillers soluble | 5.0 |
| OM peptone | 5.0 |
| Debittered yeast | 5.0 |
| Corn starch | 20.0 |
| $CaCO_3$ | 1.0 |
| $K_2HPO_4$ | 1.0 |

-continued

| | |
|---|---|
| SAG 4130 Antifoam (Union Carbide) | 0.1 |
| The pH of the medium is adjusted to 7.0 with NaOH before sterilization for 1¼ hours with 60 lb/in² steam. | |

The inoculated medium is aerated with compressed air at a rate of 3 cubic feet per minute and is stirred with agitators at 280 rpm. The fermentation is carried out at 28° C. for 5 days.

EXAMPLE 3

Isolation of Antibiotic X-14873-Na salt from Shake Flask Fermentation of Example 1

Step A

The whole broth from four six-liter Erlenmeyer flasks each containing 1.25 liters, after 5 days of fermentation was extracted twice with equal volume of ethyl acetate. After stirring for one half hour, solvent layer was separated and concentrated to an oil (3 g) under reduced pressure. The oil was dissolved in methylene chloride and was chromatographed on a methylene chloride slurry packed 150 g silica gel (Davison grade 62) column. The column was eluted with a gradient between 4 liters of methylene chloride to 4 liters of hexane/acetone (7/3) and then 3 liters of methylene chloride/methyl alcohol (8/2). Fractions of forty ml each were collected and from fraction numbers 181–480 were pooled, solvent was removed under reduced pressure, and the (1.20 g) residue thus obtained was dissolved in ethyl acetate and was chromatographed on an ethyl acetate slurry packed 50 g silica gel (Davison grade 62) column. The column was eluted with a gradient between 4 liters ethyl acetate/hexane (7/3) to 4 liters ethyl acetate and then 2 liters methylene chloride/methyl alcohol (8/2). Fractions of forty ml each were collected and from fraction number 41–160 were pooled, solvent was removed under reduced pressure, and the residue thus obtained was dissolved in ethyl acetate and was washed with equal volume of 1 N HCl two times, followed by washing with equal volume of $Na_2CO_3$ (saturated at room temperature) two times. The solvent phase was dried over $Na_2SO_4$. Solvent was removed under reduced pressure and crystallization from acetonitrile yielded antibiotic X-14873A-Na salt Mp. 154° C.

Microanalysis: calcd for $C_{35}H_{61}O_{11}Na$ (680.87): calcd: %C, 61.73; %H, 9.05; %Na, 3.38; found: %C, 61.90; %H, 9.01; %Na, 3.11; $[\alpha]_D^{25} -4.5°$ ($CHCl_3$, 1%), $-2.6°$ ($CH_3OH$, 1%).

EXAMPLE 4

Isolation of Antibiotic X-14873A-Na Salt and actinomycins X-14873B, X-14873C and X-14387D from Tank Fermentation of Example 2

Step A

To the whole broth from two sixty gallons (475 liters) fermentation was added, after 118 hrs. growth, consecutively twice one half volume of methylene chloride. After stirring for one hour, the solvent layer was separated. Two half volumes of methylene chloride extracts were pooled and were washed twice with one half volume of 1 N HCl, followed by washing with one half volume of 1 N NaOH, followed by washing with equal volume of deionized water. The solvent phase was then concentrated to an oil under reduced pressure. The 336 g oil was dissolved in n-hexane and was extracted once with acetonitrile. A precipitate was obtained. This was dissolved in water and was extracted with equal volume of methylene chloride. This methylene chloride phase was evaporated to dryness in reduced pressure and the resulting 35 g solids were dissolved in 200 ml of acetone/acetonitrile (60/40) and was chromatographed in the Waters Prep LC ™/System 500 using two 370 g Prep PAK-500/$C_{18}$ column with acetonitrile/water (80/20) elution. Fractions of 200 ml each were collected and from fraction numbers 3-5 and 10-14 were pooled.

Step B

The acetonitrile extract of Example 4/Step A was evaporated under reduced pressure and 18 g of the 89 g residue was dissolved in 150 ml of acetonitrile and was chromatographed on the Waters Prep LC ™/System 500 using one Prep PAK-500/$C_{18}$ column, with acetonitrile/water (9/1) elution. Fractions of 200 ml each were collected and from fraction numbers 1-3 and 4-7 were pooled. 71 g of the 89 g residue of the acetonitrile extract was dissolved in methyl alcohol and was chromatographed on a Sephadex LH-20 gel column with methyl alcohol. Fractions of 40 ml each were collected and fraction numbers 60-200 were pooled, solvent was removed under reduced pressure, and the 45 g residue thus obtained was dissolved in acetone/acetonitrile (60/40) and was chromatographed on the Waters Prep LC ™/System 500 using two 370 g Prep PAK-500/$C_{18}$ column with acetonitrile/water (80/20). Fractions of 100 ml each were collected, and fraction numbers 2-4, 5-8, 9-11 and 12-18 were pooled.

Step C

Fractions 10-14 of Example 4/Step A, fraction B 4-7 and 12-18 of Example 4/Step B were pooled. The solvent was removed in reduced pressure and the 19.3 g residue thus obtained was dissolved in methylene chloride and was subjected to chromatography on a methylene chloride slurry packed 600 g silica gel (Davison grade 62) column. The column was eluted with 3 liters of methylene chloride and then a gradient between 6 liters of methylene chloride to 6 liters of methylene chloride/methyl alcohol (95/5). Fractions of forty ml each were collected and fraction numbers 289-360 were pooled. The solvent was removed under reduced pressure and crystallization from acetonitrile yielded antibiotic X-14873A-Na salt. Mp. 152° C.

Microanalysis: Calcd for $C_{35}H_{61}O_{11}Na$ (680.87): calcd: %C, 61.73; %H, 9.05; %Na, 3.38; found: %C, 61.08; %H, 9.24; %Na, 3.15; $[\alpha]_D^{25} -5.4°$ ($CHCl_3$, 1%).

Step D

Fractions 3-5 of Example 4/Step A, fractions 1-3 of Example 4/Step B, and fractions 2-4 of Example 4/Step B (of the two HPLC run) were pooled. Solvent was removed under reduced pressure and the 21 g residue thus obtained was triturated with diethyl ether. 14 g diethyl ether insoluble solids were filtered off and were chromatographed on a methylene chloride slurry packed silica gel (Davison grade 62) column. The column was eluted with a gradient between 6 liters methylene chloride and 8 liters methylene chloride/ethyl alcohol/hexane (95/5/10) and then with 2 liters methylene chloride/ethyl alcohol (95/5) and 2 liters chloroform/acetone/methyl alcohol (1/1/0.1). Fractions of forty ml each were collected. Fraction numbers 342-410; 423-466 and 620-646 were pooled. Each pool was concentrated in reduced pressure, and by the addition of diethyl ether, orange precipitates of actinomycin X-14873-B (1.4 g), actinomycin X-14873-C (1.2 g) and actinomycin X-14873-D (3.9 g) were obtained. Actinomycin X-14873-B, -C and -D are distinguishable on silica gel TLC plate using methylene chloride/ethyl alcohol/n-hexane (9/1/1).

Microanalysis:
Actinomycin X-14873-B; Found %C, 57.42, 57.37; %H, 6.98, 7.00; %N, 12.75, 12.67; $[\alpha]_D^{25} -244.5°$ (MeOH, 1%) $-349.6°$ ($CHCl_3$, 1%)
Actinomycin X-14873-C: Found %C, 58.12, 57.97; %H, 7.06, 7.01; %N, 13.00, 12.95; $[\alpha]_D^{25} -299.1°$ (MeOH, 1%) $-395.2°$ ($CHCl_3$, 1%)
Actinomycin X-14873-D: Found %C, 56.50, 56.49; %H, 6.80. 7.00; %N, 12.06, 12.16; $[\alpha]_D^{25} +11°$ (MeOH, 0.2%), $-145.5°$ ($CHCl_3$, 1%)

Mass spectral analysis by fast atom bombardment of actinomycins X-14873C and X-14873D has confirmed that the two antibiotics are isomeric, with a molecular formula of $C_{61}H_{86}N_{12}O_{18}$ (m.w. 1275.44), calcd %C, 57.44; %H, 6.80; %N, 13.18. These results confirm the novelty of X-14873C and D which, like X-14873B, give on hydrolysis inter alia, both proline and 3-hydroxy-5-methylproline, clearly distinguishing all three from any known actinomycin.

Activities of the three actinomycins are:

| Antibiotic | | Acute Mouse $LD_{50}$ (mg/kg) | | Antitumor vs. S-180 tumor implant In Mice (mg/kg) | |
|---|---|---|---|---|---|
| | | i.p. | p.o. | active level | toxic level |
| Actinomycin X-14873 | B | 0.16 | 2.9 | 0.048 | 0.096 |
| | C | >1000 | | | 6.25 |
| | D | 71 | >1000 | 6-12 | 25 |

In addition, actinomycin X-14873B was active in vivo as a coccidiostat in poultry. This is the first time such activity has been observed for an actinomycin.

EXAMPLE 5

The Streptomyces X-14873 culture is grown and maintained on a starch-casein agar slant having the following composition (grams/liter distilled water):

| Soluble starch | 10.0 |
|---|---|
| Casein | 1.0 |
| $K_2HPO_4$ | 0.5 |
| $MgSO_4$ (anhydrous) | 0.5 |
| Agar | 20.0 |
| The medium pH is adjusted to 7.4 with NaOH before autoclaving. | |

The slant is inoculated with X-14873 culture and incubated at 28° C. for 7-14 days. A chunk of agar containing spores and mycelia from the sporulated culture slant is used to prepare vegetative inoculum by inoculating a 500-ml Erlenmeyer flask containing 100 ml of inoculum medium having the following composition (grams/liter distilled water):

| Tomato pomace | 5.0 |
|---|---|
| Distillers soluble | 5.0 |
| OM peptone | 5.0 |
| Debittered yeast | 5.0 |
| Eclipse N starch | 20.0 |
| $CaCO_3$ | 1.0 |
| $K_2HPO_4$ | 1.0 |
| pH is adjusted to 7.0 before sterilization. | |

The inoculated medium is incubated at 28° C. for 4 days on a rotary shaker, operating at 250 rpm with a 2-inch stroke.

A 10-ml portion of this culture is used to inoculate a 6-liter Erlenmeyer flask containing 2 liters of inoculum medium having the same composition described above.

The inoculated medium in the 2-liter Erlenmeyer flask is incubated for 3 days at 28° C. on a rotary shaker operating at 250 rmp.

Six liters of the resulting culture broth are then used to inoculate a 100-gallon fermentor containing 60 gallons of the same inoculum medium described above. The medium in the fermentor is supplemented with 0.1 gram per liter of antifoam SAG 4130 (Union Carbide) and sterilized for 1¼ hours with 60 lb/in² steam.

The inoculated fermentor is aerated with compressed air at a rate of 3 cubic feet per minute and is stirred with agitators at 220 rpm. After 3 days of incubation, 11 gallons of the resulting fermentation broth are used to inoculate 360 gallons of the following medium in a 500-gallon fermentor (grams/liter tap water):

| | |
|---|---|
| Cerelose | 20.0 |
| Peptone (Special R) (Wilson) | 5.0 |
| NaCl | 5.0 |
| CaCO₃ | 2.0 |
| Na-propionate | 1.0 |
| SAG 4130 Antifoam, (Union Carbide) | 0.1 |
| Adjust pH to 7.2 with NaOH before sterilization for 45 minutes with 60 lb/in² steam. | |

The inoculated medium in the fermentor is aerated with compressed air at 20 cubic feet per minute, and is stirred with agitators at 280 rpm. The fermentation is carried out at 28° C. for 139 hours.

EXAMPLE 6

Isolation of Antibiotic X-14873G from Tank Fermentation of Streptomyces Culture X-14873

Step A

To the whole broth of a 350 gallon (1330 liters) fermentation was added after 139 hrs growth an equal volume of ethyl acetate. After stirring for one hour, the solvent layer was separated and concentrated to 5.75 liters under reduced pressure, and was washed in turn with 1 N HCl, saturated Na₂CO₃ and deionized water.

The solvent phase was then concentrated until crude antibiotic X-14873A-Na crystallized out. The mother liquor was concentrated to an oil under reduced pressure. The oil was redissolved in methylene chloride and was chromatographed on a methylene chloride slurry packed 4 kg silica gel (Davison grade 62) column. The column was eluted with a gradient between 2 liters of methylene chloride and 6 liters hexane-methylene chloride (1/1), followed by 8 liters hexane-acetone (9/1). Fractions of 500 ml each were collected, and fraction numbers 1-4 and 5-8 were pooled.

Step B

The pooled fractions 1-4 of Step A were evaporated to dryness (81 g) under reduced pressure and were redissolved in methylene chloride and rechromatographed on a methylene chloride slurry packed 700 g silica gel column. The column was eluted with a gradient between 3 liters methylene chloride-hexane (1/1) to 4 liters hexane-acetone (95/5), followed by 7 liters hexane-acetone (9/1). Fractions of 40 ml each were collected and fraction numbers 52-310 and 320-390 were pooled. The solvent was removed under reduced pressure and crystallization of the pool 320-390 from diethyl ether-hexane yielded antibiotic X-14873G. Mp. 152°-3° C.

Microanalysis calcd. for $C_{34}H_{60}O_8$ (596.82): Calcd: %C, 68.42; %H, 10.13; Found: %C, 68.28; %H, 10.10; $[\alpha]_D^{25} + 5.5°$ (CHCl₃, 1%).

Step C

The pooled fractions 5-8 of Step A were evaporated to dryness under reduced pressure, and the residue (80 g) was redissolved in methylene chloride and was rechromatographed on a methylene chloride slurry packed 1 kg silica gel column. The column was eluted with a gradient between 4 liters methylene chloride and 8 liters hexane-acetone (9/1), followed by 6 liters hexane-acetone (8/2), 3 liters hexane-acetone (6/4) and 3 liters methylene chlorideacetone (8/2). Fractions of 40 ml each were collected. Fraction numbers 115-160, 161-182 and 183-270 were pooled, and solvent was removed under reduced pressure. Crystallization from methylene chloride-hexane of the residue of pool 115-160 yielded additional antibiotic X-14873G. Crystallization from methylene chloride-hexane of the residue of pool 183-270 yielded antibiotic X-14873H. Mp. 145°-6° C.

Microanalysis calcd for $C_{34}H_{62}O_9$ (614.84): Calcd: %C 66.41; %H, 10.16; Found:

| % C, 66.43; | % H, 9.92 |
|---|---|
| 66.55 | 9.95 |

$[\alpha]_D^{25} - 5.3°$ (CHCl₃, 1%) $+3.6°$ (CH₃OH, 1%).

The pooled fractions 161-182 contained a mixture of antibiotics X-14873G and -H.

EXAMPLE 7

Preparation of the Thallium Salt of Antibiotic X-14873A

A solution of Antibiotic X-14873A-Na salt in methylene chloride was washed with 1 N HCl, followed by water wash, then four times with an aqueous solution of thallium hydroxide. The solvent phase was concentrated, and by the addition of n-hexane crystalline thallium salt of Antibiotic X-14873A was recovered. Mp. 154° C.

Microanalysis: calcd for $C_{35}H_{61}O_{11}Tl$ (862.25): %C, 48.76; %H, 7.13; %Tl, 23.7; Found: %C, 49.01; %H, 7.07; %Tl, 21.91.

The structure of Antibiotic X-14873A was determined by X-ray analysis of the thallium salt.

EXAMPLE 8

Preparation of the Calcium Salt of Antibiotic X-14873A

A solution of Antibiotic X-14873A-Na salt in methylene chloride was washed with 1 N HCl, followed by aqueous Ca(OH)₂ and water wash. Solvent phase was concentrated in reduced pressure and was crystallized by the addition of n-hexane. Mp. 133° C.

Microanalysis: Calcd for $(C_{35}H_{61}O_{11})_2Ca$ (1355.84): %C, 62.01; %H, 9.07; %Ca, 2.96; Found: %C, 62.17; H%, 9.28; %Ca, 2.96; $[\alpha]_D^{25}$ 3.5° (MeOH, 1%), 9.99° (CHCl₃, 1%).

Antibiotic X-14873A exhibits an oral toxicity (LD₅₀) in mice of 120 mg/kg (24 hours); X-14873G exhibits an oral toxicity (LD₅₀) in mice of 4000 mg/kg (24 hours);

and X-14873H exhibits an oral toxicity ($LD_{50}$) in mice of 4000 mg/kg (24 hours).

Antibiotics exhibit some, albeit limited, activity against a variety of bacteria and dermatophytes as indicated in the tables below.

| Name of Organism | Minimum Inhibitory Concentration (mcg/ml) X-14873A |
|---|---|
| Staphylococcus aureus Smith | 64 |
| Escherichia coli 257 | 128 |
| Salmonella typhi P58A | 128 |
| Klebsiella pheumoniae A | 128 |
| Proteus mirabilis 190 | 128 |
| Pseudomonas aeruginosa B | 128 |
| Serratia marcescens SM | 128 |
| Enterobacter cloacae 5699 | 128 |
| Trichophyton mentagrophytes | 100 |
| Microsporum audouini | 100 |

| Name of Organism | ATCC Number | Minimum Inhibitory Concentration (mcg/ml) | | |
|---|---|---|---|---|
| | | X-14873A | X-14873H | X-14873G |
| Streptococcus faecium | 8043 | 0.1 | 2 | 63 |
| Staphylococcus aureus | 6538P | 6.3 | 8 | >1000 |
| Sarcina lutea | 9341 | 3.0 | 16 | >1000 |
| Bacillus megaterium | 8011 | 3.0 | 4 | >1000 |
| Bacillus sp. E | 27359 | 0.8 | 2 | 8 |
| Bacillus subtilis | 558* | 3.0 | 16 | >1000 |
| Bacillus sp. TA | 27860 | 3.0 | 8 | >1000 |
| Mycobacterium phlei | 355 | 3.0 | >1000 | >1000 |
| Streptomyces cellulosae | 3313 | 12.5 | >1000 | >1000 |
| Paecilomyces varioti | 25820 | 125 | >1000 | >1000 |
| Penicillum digitatum | 26821 | 500 | >1000 | >1000 |
| Candida albicans | 477* | 62.5 | >1000 | >1000 |
| Saccharomyces cerevisiae | 4226 | 500 | >1000 | >1000 |

*NRRL number

As indicated above, antibiotics A, G and H possess the property of adversely affecting the growth of certain gram-positive bacteria. They are, therefore, useful in wash solutions for sanitary purposes, as in the washing of hands and the cleaning of equipment, floors or furnishings of contaminated rooms or laboratories.

Antibiotic X-14873A has also been found to exhibit activity as a growth promotant in ruminants, i.e., animals with a rumen function-for example, cattle. A discussion of the mechanism whereby feed is digested, degraded and metabolized in a ruminant animal can be found in U.S. Pat. No. 3,839,557, issued Oct. 1, 1974, which discloses the use of certain antibiotics in improving ruminant feed utilization and is incorporated herewith by reference. Economically important ruminant animals include cattle, sheep and goats.

The effectiveness of Antibiotic X-14873A in modifying the ratio of volatile fatty acids produced in the rumen (and thereby improve ruminant feed utilization) is demonstrated by means of the in vitro testing.

Rumen fluid is obtained from a steer with a fistulated rumen. The steer is maintained on the following ration:
Corn: 89.93%
Alfalfa meal: 5.000%
Soy bean oil meal: 3.00%
Limestone: 0.80%
NaCl: 0.60%
Dicalcium phosphate: 0.50%
Trace minerals: 0.025%
Vitamin premix additions: 0.1%
  Vitamin A, TIU: 4.0003
  Vitamin $D_3$, IU: 0.801
  Vitamin E, TIU: 3.002

The rumen fluid is immediately strained through a #30 mesh sieve. For each fermentation, 75 ml of the resulting fluid is added to a 250 ml flask containing the following:
1 g of 80%:20% finely ground grain: hay ration;
1 ml of an 18% aqueous glucose solution (1 millimole per flask);
1.5 ml of a 3.1% aqueous urea solution (0.76 millimole per flask);
60 micromoles of each of the 10 essential amino acids (arginine, histidine, leucine, methionine, threonine, valine, lysine, isoleucine, phenylalanine, tryptophan);
1 ml of an aqueous solution of test drug to give either 10 or 25 ug/ml (calculated total volume of fermentation mixture of 80 ml);

Each flask is incubated at 38° C. in a shaking water bath equipped with a gassing hood. Carbon dioxide is continuously passed through the hood. After four hours incubation, a 10 ml quantity of the fermentation fluid is centrifuged at 14,000 rpm (approximately 30,000 xg) for 20 minutes in an International Centrifuge equipped with a No. 874 angle head. Three ml of the supernate is added to 1 ml of a 25% metaphosphoric acid solution containing 23 micromoles 2-methyl valeric acid as an internal standard. The resulting fluid is permitted to sit at room temperature for 30 minutes. The fluid is filtered through a 0.22 millimicron Millipore filter and refrigerated until gas-liquid chromatographic analyses for volatile fatty acids.

Gas-liquid chromatographic (GLC) analyses of one nonmedicated control fermentation and two fermentations, one with Antibiotic X-14873A and the other lasalocid, are set forth in the following table. The antibiotics are included in the rations at a concentration of 30 g/ton.

| Experiment Day | VFA Ratio:[a] $C_3/(C_2 + nC_4)$ Experimental Groups | | |
|---|---|---|---|
| | Nonmedicated[b] | Lasalocid,[c] 30 g/ton | X-14873A[c] 30 g/ton |
| Pre-medication | | | |
| 1 | 0.262 ± 0.065 | 0.229 ± 0.013 | 0.213 ± 0.016 |
| 3 | 0.260 ± 0.050 | 0.255 ± 0.051 | 0.235 ± 0.036 |
| 5 | 0.240 ± 0.024 | 0.244 ± 0.060 | 0.234 ± 0.042 |
| 8 | 0.240 ± 0.042 | 0.236 ± 0.041 | 0.245 ± 0.046 |
| 10 | 0.206 ± 0.037 | 0.224 ± 0.011 | 0.216 ± 0.038 |
| Medication | | | |
| 2 | 0.211 ± 0.019 | 0.376 ± 0.109 | 0.445 ± 0.075 |
| 5 | 0.248 ± 0.058 | 0.390 ± 0.073 | 0.584 ± 0.328 |
| 7 | 0.325 ± 0.166 | 0.373 ± 0.015 | 0.679 ± 0.448 |

| | VFA Ratio:[a] $C_3/(C_2 + nC_4)$ Experimental Groups | | |
|---|---|---|---|
| Experiment Day | Nonmedicated[b] | Lasalocid,[c] 30 g/ton | X-14873A[c] 30 g/ton |
| 9 | 0.338 ± 0.164 | 0.381 ± 0.064 | 0.642 ± 0.387 |
| 12 | 0.293 ± 0.148 | 0.372 ± 0.056 | 0.495 ± 0.242 |

[a] ± one standard deviation.
[b] 4 animals.
[c] 3 animals.

As shown in the above Table, the ratio of propionate ($C_3$) to acetate ($C_2$) and n-butyrate ($nC_4$) is significantly improved. With the increase of propionates rather than acetates from the carbohydrates, the efficiency of carbohydrate and therefore feed utilization is increased. Also, it is shown that Antibiotic X-14873A elicited a greater increase over control of the volitile fatty acid ratio than lasalocid, an active compound.

Administration of Antibiotic X-14873A, hereafter "antibiotic" or "antibiotic compound" prevents and treats ketosis as well as improves feed utilization. The causative mechanism of ketosis is a deficient production of propionate compounds. A presently recommended treatment is administration of propionic acid or feeds which preferentially produce propionates. It is obvious that encouraging propionate production from ordinary feeds will reduce incidence of ketosis.

It has been found that Antibiotic X-14873A increases the efficiency of feed utilization in ruminant animals when it is administered orally to the animals. The easiest way to administer the antibiotic is by mixing it in the animal's feed.

However, the antibiotic can be usefully administered in other ways. For example, it can be incorporated into tablets, drenches, boluses, or capsules, and dosed to the animals. Formulations of the antibiotic compound in such dosage forms can be accomplished by means of methods well-known in the veterinary pharmaceutical art.

Capsules are readily produced by filling gelatin capsules with any desired form of the desired antibiotics. If desired, the antibiotic can be diluted with an inert powdered diluent, such as a sugar, starch, or purified crystalline cellulose in order to increase its volume for convenience in filling capsules.

Tablets of the antibiotic are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents again include starch and lactose, while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps and polyethylene glycol.

The administration of the antibiotic compound may be as a slow-pay-out bolus. Such boluses are made as tablets except that a means to delay the dissolution of the antibiotic is provided. Boluses are made to release for lengthy periods. The slow dissolution is assisted by choosing a highly water-insoluble form of the antibiotic. A substance such as iron filing is added to raise the density of the bolus and keep it static on the bottom of the rumen.

Dissolution of the antibiotic is delayed by use of a matrix of insoluble materials in which the drug is inbedded. For example, substances such as vegetable waxes, purified mineral waxes, and water-insoluble polymeric materials are useful.

Drenches of the antibiotic are prepared most easily by choosing a water-soluble form of the antibiotic. If an insoluble form is desired for some reason, a suspension may be made. Alternatively, a drench may be formulated as a solution in a physiologically acceptable solvent such as a polyethylene glycol.

Suspensions of insoluble forms of the antibiotic can be prepared in nonsolvents such as vegetable oils, e.g., peanut, corn or sesame oil; in a glycol such as propylene glycol or a polyethylene glycol; or in water, depending on the form of the antibiotic chosen.

Suitable physiologically acceptable adjuvants are necessary in order to keep the antibiotic suspended. The adjuvants can be chosen from among the thickeners, such as carboxymethylcellulose, polyvinylpyrrolidone, gelatin, and the alginates. Many classes of surfactants serve to suspend the antibiotic. For example, lecithin, alkylphenol polyethylene oxide adducts, naphthalenesulfonates, alkylbenzenesulfonates, and the polyoxyethylene sorbitan esters are useful for making suspensions in liquid nonsolvents.

In addition, many substances which effect the hydrophilicity, density, and surface tension of the liquid can assist in making suspensions in individual cases. For example, silicone anti-foams, glycols, sorbitol, and sugars can be useful suspending agents.

The suspendable antibiotic may be offered to the grower as a suspension, or as a dry mixture of the antibiotic and adjuvants to be diluted before use.

The antibiotic may also be administered in the drinking water of the ruminants. Incorporation into drinking water is performed by adding a water-soluble or water-suspendable form of the antibiotic to the water in the proper amount. Formulation of the antibiotic for addition to drinking water follows the same principles as formulation of drenches.

The most practical way to treat animals with the antibiotic compound is by the formulation of the compound into the feed supply. Any type of feed may be medicated with the antibiotic compounds, including common dry feeds, liquid feeds and pelleted feeds.

The methods of formulating drugs into animal feeds are well-known. It is usual to make a concentrated drug premix as a raw material for medicated feeds. For example, typical drug premixes may contain from about one to about 400 grams of drug per pound of premix. The wide range results from the wide range of concentration of drug which may be desired in the final feed. Premixes may be either liquid or solid.

The formulation of ruminant feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound or of premix, in the feed.

All of the methods of formulating, mixing and pelleting feeds which are normally used in the ruminant feed art are entirely appropriate for manufacturing feeds containing the antibiotic compound.

As has been shown, oral administration of the antibiotic beneficially alters the production of propionates relative to the production of acetates in the rumen. It may therefore be postulated that the same treatment would also benefit monogastric animals which ferment fibrous vegetable matter in the cecum, since it would be expected that a beneficial change in the propionate/acetate ratio would occur upon oral administration of the instant antibiotic. Horses, swine and rabbits are exemplary animals which digest a part of their food by cecal fermentation.

Antibiotic X-14873A also has demonstrated activity as an agent in the treatment or prevention of swine dysentery. The compound was examined for activity against *Treponema hyodysenteriae*, the etiologic agent of swine dysentery. The compound exhibited a minimum inhibitory concentration of 5 mcg/ml.

Antibiotic X-14873 also exhibits activity as a coccidio-static agent, exhibiting in vitro activity against *E. tenella* at 200 ppm.

What is claimed:

1. A compound of the formula

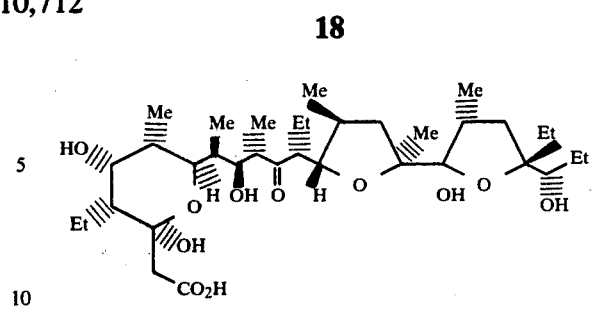

and the pharmaceutically acceptable salts thereof.

2. A compound of the formula

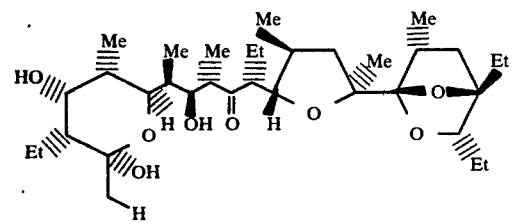

3. A compound of the formula

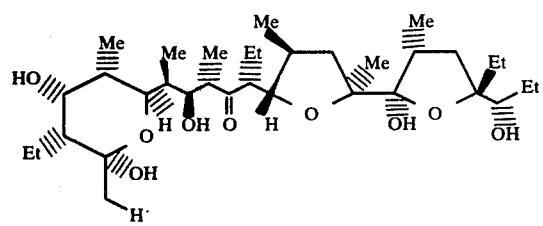

* * * * *